(12) United States Patent
Nassar et al.

(10) Patent No.: US 6,865,955 B2
(45) Date of Patent: Mar. 15, 2005

(54) CONVEYOR DIAGNOSTIC SYSTEM

(75) Inventors: Sayed Nassar, Northville, MI (US); Gerry Grzadzinski, Sterling Heights, MI (US); Sherif Gindy, Macomb, MI (US)

(73) Assignee: DaimlerChrysler Corporation, Auburn Hills, MI (US)

( * ) Notice: Subject to any disclaimer, the term of this patent is extended or adjusted under 35 U.S.C. 154(b) by 82 days.

(21) Appl. No.: 10/452,881

(22) Filed: Jun. 2, 2003

(65) Prior Publication Data

US 2004/0237662 A1 Dec. 2, 2004

(51) Int. Cl.⁷ ................................................ G01N 3/08
(52) U.S. Cl. ...................................................... 73/828
(58) Field of Search .................... 73/862.391, 862.392, 73/828, 862.451, 784; 198/867.01, 349.95, 708; 702/97; 177/119

(56) References Cited

U.S. PATENT DOCUMENTS

| | | | | |
|---|---|---|---|---|
| 4,274,783 A | * | 6/1981 | Eineichner et al. | 414/134 |
| 4,566,339 A | * | 1/1986 | Davidson et al. | 73/862.39 |
| 4,977,783 A | * | 12/1990 | Pratt | 73/862.39 |
| 5,272,924 A | * | 12/1993 | Tassic et al. | 73/862.391 |
| 5,287,756 A | | 2/1994 | Tassic | |
| 5,582,287 A | * | 12/1996 | Heit et al. | 198/803.01 |
| 6,435,035 B1 | * | 8/2002 | Kubsik et al. | 73/828 |
| 6,545,231 B1 | * | 4/2003 | Hafner | 177/119 |

* cited by examiner

Primary Examiner—Edward Lefkowitz
Assistant Examiner—Octavia Davis
(74) Attorney, Agent, or Firm—Ralph E. Smith

(57) ABSTRACT

Apparatus for measuring a plurality of forces acting on a conveyor chain of a conveyor line includes a pre-selected chain link coupled to the conveyor chain, and a sensor array having a plurality of strain gauges disposed on the pre-selected chain link, each of the plurality of strain gauges being distinctly oriented to measure the plurality of forces acting on the pre-selected link.

14 Claims, 4 Drawing Sheets

US 6,865,955 B2

CONVEYOR DIAGNOSTIC SYSTEM

FIELD OF THE INVENTION

The present invention relates generally to a conveyor diagnostic system, and more particularly to a system that employs a method for measuring multi-directional forces acting on a conveyor chain.

BACKGROUND OF THE INVENTION

Most conveyor chains used for heavy duty conveyors experience a great amount of stress due to the combined effect of tension, bending, and torsion, which in turn, may cause failure in the conveyor.

In order to properly maintain and prevent failure of a conveyor chain, the chain must be continuously monitored. Current diagnostic systems monitor chain links in conveyor chains by utilizing strain gauges directly mounted to the chain links to measure the inherent tension loading acting on the conveyor chain. However, measuring the tension loading on the chain links may not be a true representation of the conditions that actually exist throughout the conveyor chain. Conveyor chains also experience other failure causing forces such as bending and twisting while moving down the conveyor line, which are not measured in current systems. Current systems also lack a practical means of providing continuous power to the system that drives the data acquisition hardware, thus resulting in frequent interruptions to the conveyor line for replacing batteries and downloading the data collected from the strain gauges. Furthermore, current systems lack effective warning signals indicating imminent failure of the conveyor chain to the conveyor operator.

Therefore, there is a need for a conveyor diagnostic system that employs a method for measuring multi-directional forces acting on a link of the conveyor chain, which is representative of the condition of the conveyer chain. In addition there is a need for a system that is capable of providing a continuous stream of real time data of the forces acting on the chain to the conveyor operator. Furthermore, there is a need for effective indicators for warning the conveyor operator of failures the chain is experiencing.

SUMMARY OF THE INVENTION

In accordance with the present invention, an apparatus for measuring a plurality of forces acting on a conveyor chain in a conveyor line is provided. The apparatus includes a pre-selected chain link coupled to the conveyor chain, and a sensor array having a plurality of strain gauges disposed on the pre-selected chain link, each of the plurality of strain gauges being distinctly oriented to measure the plurality of forces acting on the pre-selected link.

Further areas of applicability of the present invention will become apparent from the detailed description provided hereinafter. It should be understood that the detailed description and specific examples, while indicating the preferred embodiment of the invention, are intended for purposes of illustration only and are not intended to limit the scope of the invention.

BRIEF DESCRIPTION OF THE DRAWINGS

The present invention will become more fully understood from the detailed description and the accompanying drawings, wherein.

DETAILED DESCRIPTION

The following description is merely exemplary in nature and is in no way intended to limit the invention, its application, or uses.

Figure 1:
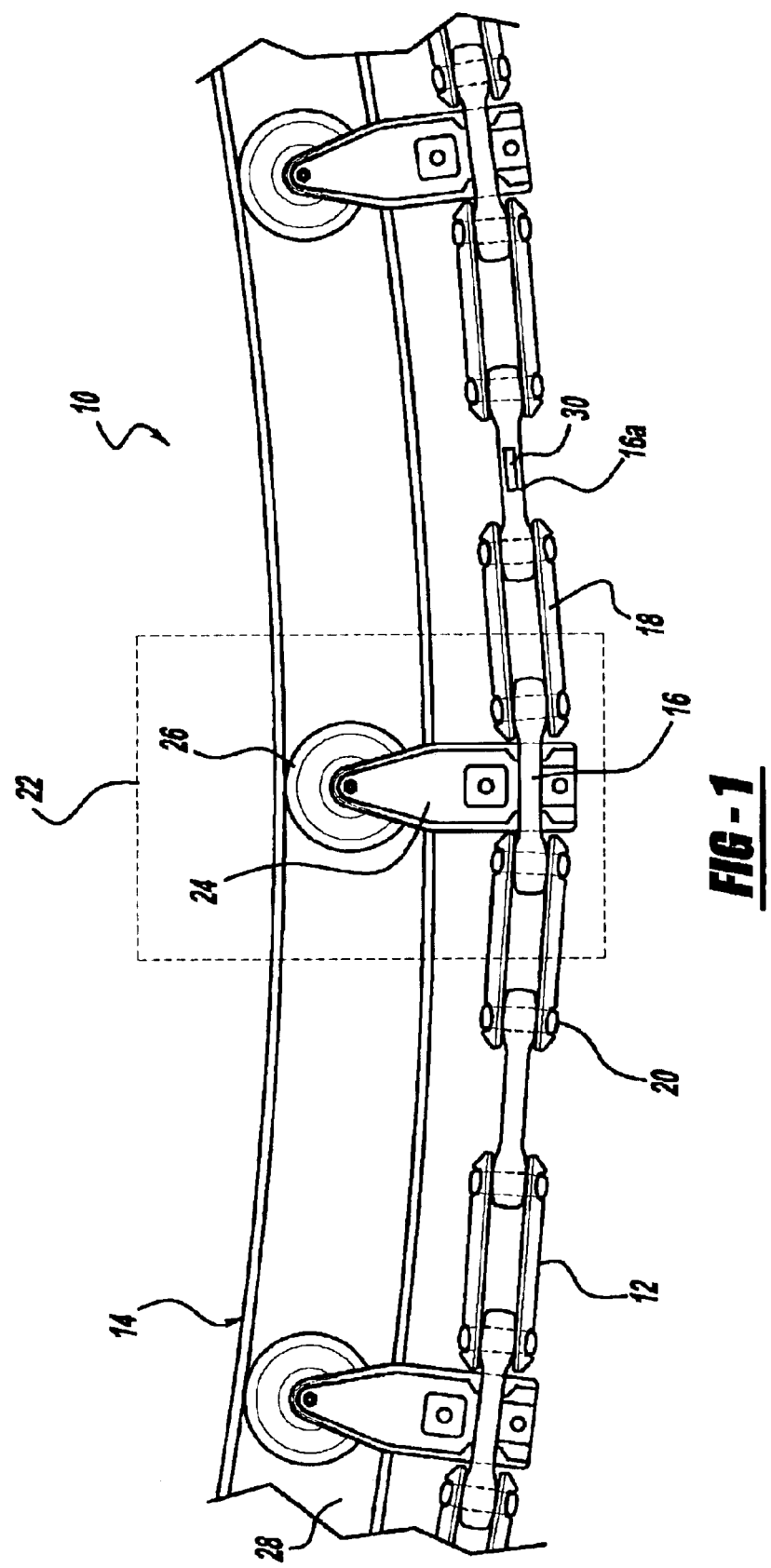
FIG. 1 is a front view of a conveyor diagnostic system.
Figure 2:
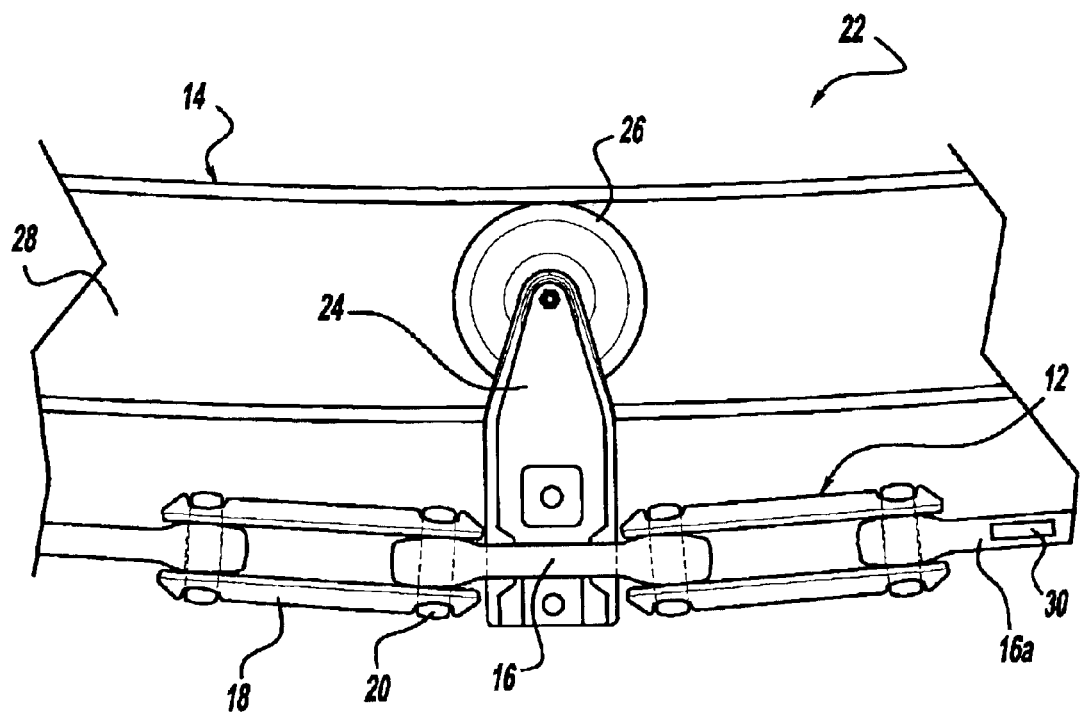
FIG. 2 is a detailed front view of a carrier assembly of an exemplary conveyor chain that can be used in accordance with the present invention.

FIGS. 1 and 2 illustrate a conveyor diagnostic system 10 for measuring a plurality of forces acting on a conveyor chain 12 as it travels through a conveyor line 14. The conveyor chain 12 generally includes single links 16 and dual links 18 coupled in an alternating manner. A connection pin 20 couples the single links 16 to the dual links 18. The conveyor line 14 includes a carrier assembly 22 for supporting the chain 12, which is better illustrated in FIG. 2. The carrier assembly 22 includes trolleys 24 having an upper portion and a lower portion. The upper portion of each trolley 24 is coupled to a roller 26 such that the trolleys 24 are supported by a horizontal beam 28. Intermediate portions of the trollies 24 are coupled to the single links 16 of the chain. The lower portions of the trollies 24 are used to support some load to be lifted and carried by the chain 12 along the conveyor line 14.

A sensor array 30 constructed in accordance with the present invention is disposed in one of the single links 16 of the conveyor chain 12. Specifically, the sensor array 30 is embedded in the center of a pre-selected chain link 16a as shown. The pre-selected chain link 16a having the sensor array 30 is manufactured differently from that of a typical single link 16 in the chain 12. Depending on the application, the sensor array 30 may be mounted anywhere along the conveyor chain 12, such as, for example, on one of the dual links 18. It should be understood that chain 12 may have more than one pre-selected chain link having the sensor array, providing an even more thorough investigation of the state of the chain 12.

Figure 3:
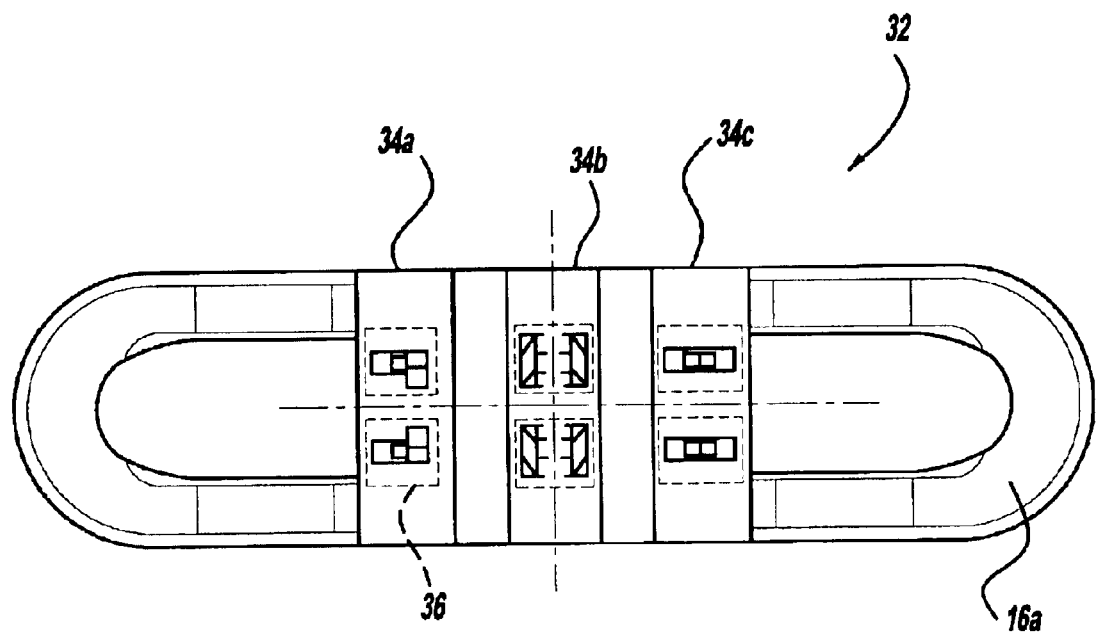
FIG. 3 is a top view of a pre-selected chain link of a conveyor chain having a sensor array for measuring a plurality of forces acting on the pre-selected chain link.

The sensor array 30 is adapted to measure a plurality of forces acting on pre-selected chain link 16a as it travels along the conveyor line 14. The sensor array 30 includes a specially designed assembly 32 as shown in FIG. 3. The specially designed assembly 32 generally comprises a plurality of sub-structures that are operative to measure the plurality of forces acting on the chain 12. Specifically, a first, second, and third sub-structure 34a, 34b, 34c respectively are coupled together and mounted on the center of pre-selected chain link 16a of the chain 12. It should be understood that the sub-structure 34a, 34b, 34c can be disposed anywhere along the pre-selected chain link 16a.

Sub-structures 34a, 34b, and 34c each comprise a plurality of packages 36 affixed to each sub-structure 34a, 34b, 34c. Each package 36 includes a circuit having a plurality of strain gauges wired into a Wheatstone Bridge. The plurality of strain gauges act as means for translating a particular mechanical load into an electrical signal linearly proportional to it. The measured forces acting on pre-selected chain link 16a are translated into signal voltages by the resistance change of the strain gauges. The scheme in which the strain gauges are wired into the Wheatstone Bridge acts, as adding and/or subtracting electrical network and allows compensation for temperature effects as well as cancellation of signals caused by extraneous loading such as the other loads measured by the other sub-structures. It should be understood that a number of stationary Wheatstone Bridges with strain gauges may be affixed at different locations of the chain 12 to provide the necessary measurements needed to determine an accurate representation of the condition of the chain 12.

The strain gauges of each sub-structure 34a, 34b, 34c are distinctly orientated, thus having each sub-structure 34a, 34b, 34c measure a distinct force acting on pre-selected chain link 16a. Specifically, the first sub-structure 34a is oriented in a tension force component direction to strictly measure tension loading. The second sub-structure 34b is oriented in a bending force component direction to strictly measure bending due to the horizontal and vertical movement of the chain 12 as the chain 12 goes through curves. The third sub-structure 34c is oriented in a twisting force component direction to strictly measure twisting due to lack of alignment of the trolleys 24 that are pulling the chain 12 and guiding it through the conveyor line 14. FIG. 3 illustrates the strain gauges of each sub-structure 34a, 34b, 34c oriented in a distinct manner. It should be understood that the strain gauges in each sub-structure 34a, 34b, 34c may be oriented to measure any of the three types of forces, such as, tension, bending, and twisting that may be acting on preselected chain link 16a. However, in order to effectively measure the three types of forces acting on pre-selected chain link 16a, the strain gauges of each sub-structure 34a, 34b, 34c should be oriented to measure a distinct force. The strain gauges for each sub-structure 34a, 34b, 34c are oriented to be sensitive enough in the direction of the force component it is measuring and stiff enough in all other directions to minimize the influence on the overall stiffness of pre-selected chain link 16a. It should be understood that the pre-selected chain link 16a is not limited to having only sub-structures 34a, 34b, and 34c, a number of sub-structures may be mounted on pre-selected chain link 16a depending on the application.

Figure 4:
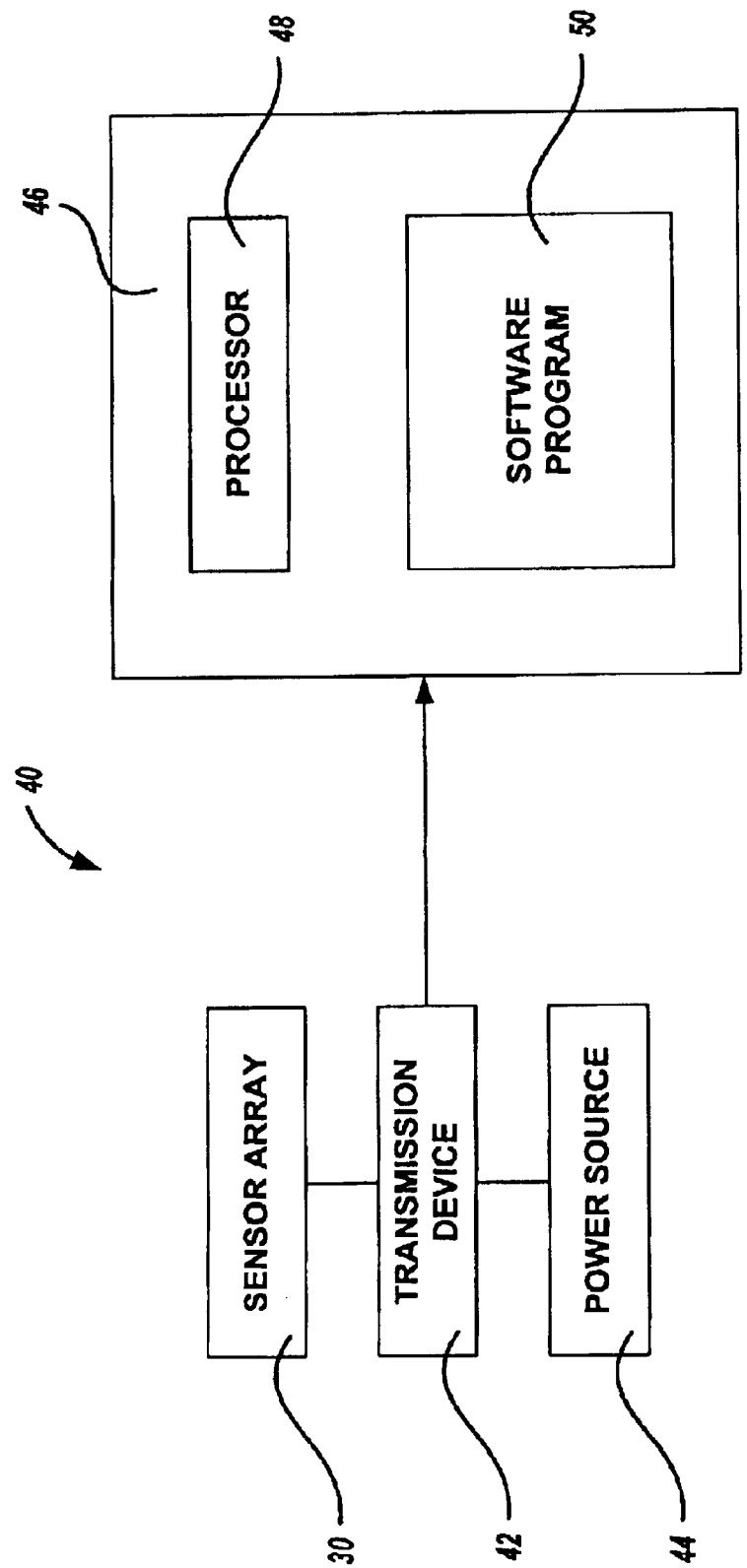
FIG. 4 illustrates a telemetry data transmission system according to the present invention.

FIG. 4 illustrates a telemetry data transmission system 40 according to the present invention. The system 40 includes the sensor array 30, a transmission device 42, a power source 44, and an external device 46 for analyzing the forces measured by the sensor array 30. The sensor array 30 is coupled to the transmission device 42. The transmission device includes a plurality of radio-frequency (RF) transmitters operative to receive each of the signals measured by the sensor array 30 and send the signals to the external device 46 for further processing. Each of the plurality of transmitters correspond to one of the sub-structures 34a, 34b, 34c, thus having each of the plurality of transmitters receive a reading from one of the sub-structures 34a, 34b, 34c. The power source 44 is coupled to both the sensor array 30 and the transmission device 42. The power source 44 drives the plurality of RF transmitters in the transmission device 42 and excites the Wheatstone Bridges in the sensor array 30 for operation. The transmission device 42 is continuously in communication with the external device 46. The external device 46 includes a stationary receiver (not shown) for receiving the readings sent by the transmission device 42. The transmission device 42 can be coupled to the external device 46 through either a wire or in a wireless manner, such as infrared. It should be understood that the conveyor line 14 includes a primary power source (not shown) coupled to the conveyor line 14 for supplying power to the line 14 in order for the conveyor chain 12 to operate.

The external device 46 includes a processor 48 with a software program 50 for determining a value representative of the current condition of the chain 12. The external device 46 is used for receiving the measured forces from the transmission device 42 and analyzing the measured forces to determine the current condition of the conveyor chain 12. Specifically, processor 48 along with the software program 50 of the external device 46 is operative to compile the readings measured from the strain gauges. As a result, a value representing the current condition of the chain 12 is determined, which will further be described below. The external device 46 includes a plurality of stored values that represent the desired condition of a typical chain in normal operating conditions. The plurality of stored values are predetermined based on prior test results showing the normal amount of tension, bending, and twisting forces that a typical chain can withstand before experiencing problems. One of the plurality of stored values is selected based on the type of conveyor being used and/or the application in use.

Figure 5:
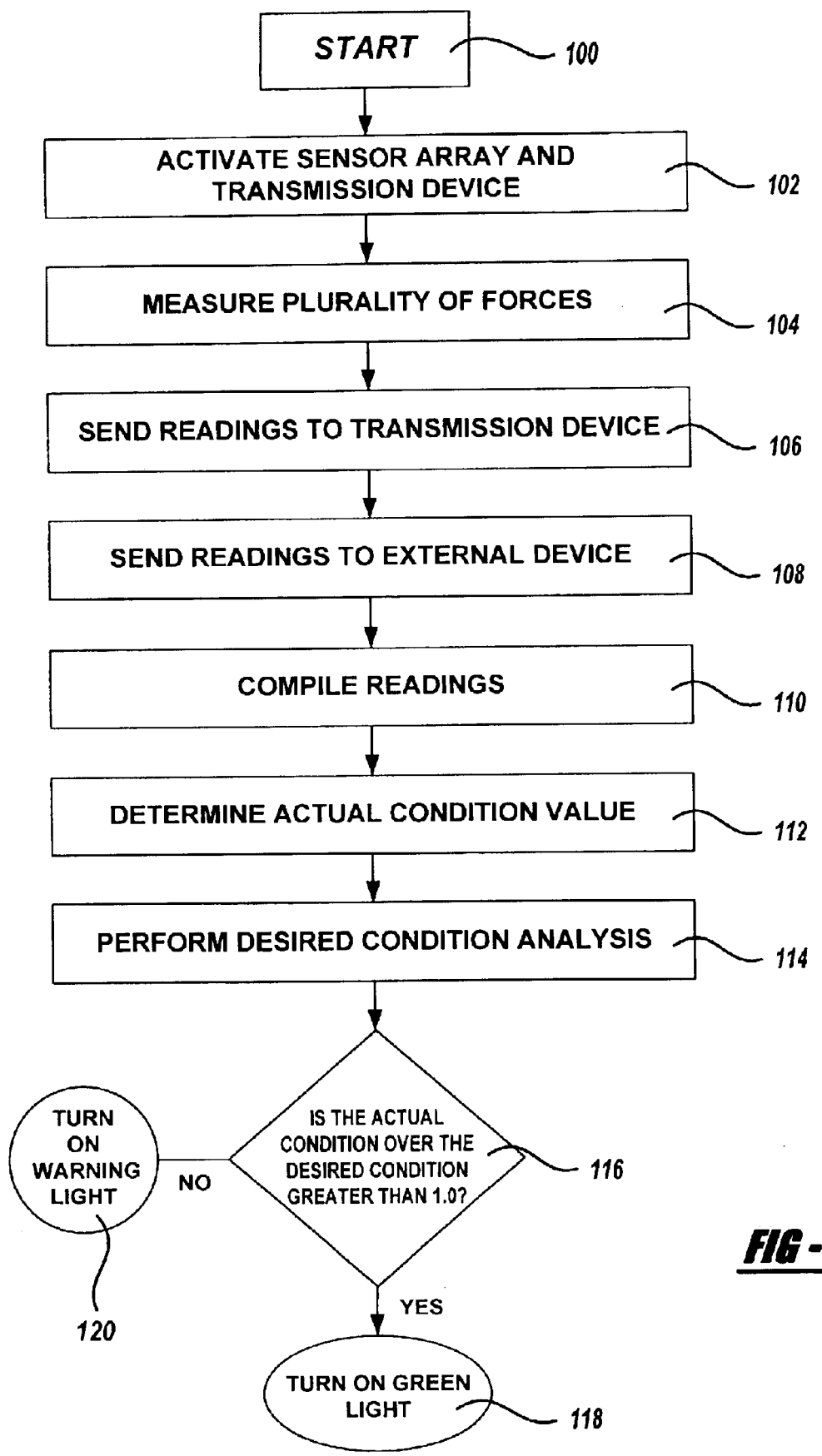
FIG. 5 is a flowchart showing the operational steps of the present invention.

FIG. 5 is a flowchart showing the operational steps of the conveyor diagnostic system 10. The conveyor diagnostic system 10 starts in step 100. In step 102, the sensor array 30 and the plurality of RF transmitters of the transmission device 42 are activated by the power source 44. In step 104, the sensor array 30 measures the plurality of forces acting on pre-selected chain link 16a of the chain 12 as the link 16a is moving along the conveyor line 14. Next, the sensor array 30 sends the readings to the transmission device 42 in step 106. In step 108, the transmission device 42 sends the readings directly to the external device 46 for further analysis. In step 110, the processor 48 along with the software program 50 takes the readings and compiles the readings together. The readings are compiled using various well known equations and theories such as, for example, Hooke's Law, which takes into account each force measured by the sensor array 30. A value representative of the current condition of the chain 12, which is referred to as the actual condition value is determined in step 112. In step 114, a desired condition analysis is performed to select one of the plurality of stored values to represent the desired condition value, which represents the desired condition of a typical conveyor of the type being used in this example while under normal operating conditions. In decision step 116, the external device 46 determines if the ratio of the actual condition value over the desired condition value is greater than 1.0. If true, then the indicator green light 118 turns on. If false, then the indicator warning light 120 turns on. This informs the user of the conveyor that the amount of forces acting on the conveyor chain 12 has exceeded the amount the chain 12 normally can withstand. The processing from steps 100 to 116 is continuous.

Alternatively, a user interface (not shown), such as, for example, a computer monitor is used to display to the conveyor operator the ratio of the actual condition value over the desired condition value. The results may be displayed graphically or numerically. However, other indicators for informing the conveyor operator may be employed, such as, for example, a buzzer. As another alternative, the external device 46 is programmed to automatically shut down the conveyor line 14 when the ratio of the actual condition value over the desired condition value is greater than 1.0.

In one aspect, the power source 44 is a solar cell, such as a photovoltaic cell, that is adapted to receive light from a plurality of light sources (not shown) mounted throughout the conveyor line 14. The utilization of the solar cell is to provide a continuous stream of real time data to the conveyor operator, thereby avoiding any interruptions throughout the manufacturing process. It should be readily understood that the broader aspects of the present invention are also applicable to other types of solar cells (e.g., polycrystalline solar cells).

In operation, pre-selected chain link 16a moves along the conveyor line 14, passing through the plurality of light sources mounted on various locations of conveyor line 14. The plurality of light sources provide continuous power to the power source 44. While pre-selected chain link 16a is passing through one of the plurality of light sources, the power source 44 incorporated into pre-selected chain link 16a is charged, continuously powering both the sensor array 30 and the transmission device 42. It should be understood that the plurality of light sources do not necessarily have to be mounted on the conveyor line 14 itself. The plurality of light sources may also be mounted anywhere around the conveyor line 14. However, the plurality of light sources need to be mounted in such a way to permit communication between the power source 44 and the plurality of light sources.

A valuable advantage to any measurement system is its ability to calibrate the system 10 of the present invention at all times, without requiring any additional equipment, setup, or interruption of the manufacturing process. The present invention allows for continuous analysis of a conveyor chain while in operation. In addition, the present invention now provides a true representation of the actual condition of a conveyor chain while in operation by measuring tension, bending, and twisting forces. As such, the conveyor operator will be provided a proper response time, which decreases the chances for failure in the conveyor.

The description of the invention is merely exemplary in nature and, thus, variations that do not depart from the gist of the invention are intended to be within the scope of the invention. Such variations are not to be regarded as a departure from the spirit and scope of the invention.

What is claimed is:

1. An apparatus for measuring a plurality of forces acting on a conveyor chain of a conveyor line comprising:
    a pre-selected chain link coupled to the conveyor chain;
    a sensor array having a plurality of strain gauges mounted on the pre-selected chain link, the plurality of strain gauges being distinctly oriented to measure each of the plurality of forces acting on the pre-selected link,
    wherein the plurality of strain gauges includes at least one gauge for measuring bending force.

2. The apparatus of 1, further comprising:
    a transmission device coupled to the sensor array operative to receive readings of each of the plurality of forces acting on the pre-selected link from the sensor array; and
    an external device having a processor operative to receive the readings from the transmission device and to determine a value representative of a current condition of the conveyor chain.

3. The apparatus of claim 2, wherein the transmission device comprises at least one transmitter for receiving the readings from the sensor array and sending the readings to the external device.

4. The apparatus of claim 2, further comprising a power source coupled to the sensor array and the transmission device, the power source operative to supply power to the sensor array and the transmission device.

5. The apparatus of claim 4, wherein the power source comprises a solar cell.

6. The apparatus of claim 2, wherein the external device is operative to select a predetermined one of a plurality of stored condition values based on an amount of force a typical chain can withstand and to compare the value representative of a current condition to the selected predetermined condition value.

7. The apparatus of 1, wherein the plurality of strain gauges includes at least one gauge for measuring tension force.

8. The apparatus of 1, wherein the plurality of strain gauges includes at least one gauge for measuring twisting force.

9. An apparatus for measuring a plurality of forces acting on a conveyor chain of a conveyor line comprising:
    a pre-selected chain link coupled to the conveyor chain;
    a sensor array having a plurality of strain gauges mounted on the pre-selected chain link, each of the plurality of strain gauges being distinctly oriented to measure each of the plurality of forces acting on the pre-selected link,
    wherein the plurality of strain gauges includes at least one gauge for measuring twisting force.

10. The apparatus of claim 9, wherein the plurality of strain gauges includes at least one gauge for measuring bending force.

11. A method of monitoring a conveyor chain comprising:
    disposing a sensor array having a plurality of strain gauges on a pre-selected link of the conveyor chain; and
    orienting each of the plurality of strain gauges to measure one of a plurality of force components,
    wherein the plurality of force components includes tension and at least one of bending and twisting.

12. The method of 11, further comprising:
    employing a transmission device to receive readings from the sensor array;
    sending the readings from the transmission device to an external device;
    processing the readings measured by the sensor array; and
    determining a value representative of the current condition of the conveyor chain.

13. The method of claim 12, further comprising employing a power source for supplying power to the sensor array and the transmission device.

14. The method of claim 13, wherein the power source is a solar cell battery adapted to continuously be changed by a plurality of light sources.

* * * * *